(12) United States Patent
Okamura

(10) Patent No.: US 12,167,763 B2
(45) Date of Patent: Dec. 17, 2024

(54) MEDICAL HEAD-COOLING CAP SET

(71) Applicant: Hair Clinic Reve-21 Corporation, Osaka (JP)

(72) Inventor: Katsumasa Okamura, Osaka (JP)

(73) Assignee: Hair Clinic Reve-21 Corporation, Osaka (JP)

( * ) Notice: Subject to any disclaimer, the term of this patent is extended or adjusted under 35 U.S.C. 154(b) by 0 days.

(21) Appl. No.: 17/907,956

(22) PCT Filed: Jan. 15, 2021

(86) PCT No.: PCT/JP2021/001229
§ 371 (c)(1),
(2) Date: Aug. 29, 2022

(87) PCT Pub. No.: WO2021/171821
PCT Pub. Date: Sep. 2, 2021

(65) Prior Publication Data
US 2023/0015573 A1  Jan. 19, 2023

(30) Foreign Application Priority Data
Feb. 28, 2020 (JP) ................................. 2020-032962

(51) Int. Cl.
*A42B 1/008* (2021.01)
*A42B 1/017* (2021.01)

(52) U.S. Cl.
CPC .............. *A42B 1/008* (2013.01); *A42B 1/017* (2021.01)

(58) Field of Classification Search
CPC . A42B 1/008; A42B 1/017; A61F 2007/0008; A61F 7/0085
See application file for complete search history.

(56) References Cited

U.S. PATENT DOCUMENTS 5,603,728 A * 2/1997 Pachys ...................... A61F 7/02
607/104
6,277,143 B1 * 8/2001 Klatz ........................ A61F 7/00
607/104

(Continued)

FOREIGN PATENT DOCUMENTS

JP  S59-22131 U  2/1984
JP  S62-1617 U  1/1987

(Continued)

*Primary Examiner* — Jillian K Pierorazio
(74) *Attorney, Agent, or Firm* — j-pat U.S. Patent Legal Services; James W. Judge

(57) ABSTRACT

Afforded is a medical head-cooling cap set that heightens scalp-cooling efficiency and that fitted on to a user's head produces no pressuring feeling nor slips out of place. The cap set is constituted from a head-cooling cap, an inner cap, and an outer cap. Two first belts that are drawn out from either side of the outer-cap opening part and stretch to the exterior are linkable by a first fastener, and after the head has been passed into the opening and the outer cap has been donned, the belts can be fastened neck-area-forward by the fastener; meanwhile, two second belts that extend from alongside the rear part mid-brim and head front brim-ward are linkable by a second clasp, and after the head has been passed into the opening and the outer cap has been donned, the second belts can be fastened around the forehead by the clasp.

8 Claims, 5 Drawing Sheets

(56) References Cited

U.S. PATENT DOCUMENTS

| | | | |
|---|---|---|---|
| 2006/0030916 A1* | 2/2006 | Lennox | A61F 7/0085 |
| | | | 607/104 |
| 2010/0137951 A1* | 6/2010 | Lennox | A61F 7/02 |
| | | | 607/104 |
| 2010/0186436 A1* | 7/2010 | Stormby | A61F 7/10 |
| | | | 62/259.3 |
| 2016/0219965 A1* | 8/2016 | Sansone | A42B 3/285 |
| 2016/0367396 A1* | 12/2016 | Triggiano | A61F 7/10 |
| 2017/0020721 A1* | 1/2017 | Kobilca | A61F 7/02 |
| 2018/0055721 A1* | 3/2018 | Quisenberry | A61F 7/007 |
| 2019/0336330 A1* | 11/2019 | Hickey | A61F 7/10 |
| 2020/0375793 A1* | 12/2020 | Dilligan | A61F 7/0085 |
| 2021/0267792 A1* | 9/2021 | Cronin | G06F 30/00 |
| 2021/0307439 A1* | 10/2021 | Okamura | A42B 1/205 |
| 2022/0023094 A1* | 1/2022 | Dilligan | A61F 7/0085 |
| 2023/0010829 A1* | 1/2023 | Bhinder | A61F 7/0085 |

FOREIGN PATENT DOCUMENTS

| | | |
|---|---|---|
| JP | 2002-209924 A | 7/2002 |
| JP | 2015-158027 A | 9/2015 |

* cited by examiner

MEDICAL HEAD-COOLING CAP SET

TECHNICAL FIELD

The present invention relates to a head-cooling cap set—namely, a medical head-cooling cap set constituted by three items, an inner cap, a head-cooling cap, and an outer cap—which is utilized when the scalp is to be cooled in cancer treatment.

BACKGROUND ART

Chemotherapies used in cancer treatment are often accompanied by hair loss, wherein patients' psychological distress and other significant lowering of quality-of-life has been a problem. It is known that such hair loss can be prevented or suppressed by maintaining the scalp at a low temperature to keep the hair roots from absorbing the therapeutic drugs for chemotherapy. For this reason, a head cooling device directed to preventing hair loss due to chemotherapy has been proposed (reference is made to Patent Document 1). With head cooling devices of this kind, a cooling-medium flow path is formed inside a helmet-shaped component that is fitted onto a user's head, and the cooling medium is made to circulate within the cooling-medium flow path to cool the scalp by heat exchange between the scalp and the cooling medium.

The helmet-shaped component that is fitted onto the head of the user is often manufactured by molding from a synthetic resin such as a silicone rubber. Although silicone rubbers have a certain degree of flexibility, since the shape and size of users' heads vary, it is difficult to get the helmet-shaped component to fit snugly over the entire head. Since the inside surface of the helmet-shaped member functions as a heat-exchange surface, if a gap arises between the user's scalp and the inside surface of the helmet-shaped component, a portion of the scalp loses contact with the inside surface of the helmet-shaped component, leading to problems of the cooling of the scalp becoming uneven or the cooling efficiency deteriorating. As a method of reducing gaps of this sort, fitting an inner element made of a flexible material between the scalp and the helmet-shaped component in order to facilitate conforming it to the shape and size of a user's head has been carried out.

As explained above, a general head cooling device that is put on in order to cool the scalp of a cancer patient is made up of a head-cooling cap, and an inner element worn between the head-cooling cap and the scalp. Here, in order to effectively prevent hair loss on the scalp of cancer patients, the snugness of the fit of the inner element on the scalp becomes an issue. That being the case, the fact that the shape and size of the user's head are theirs individually compels having to custom-make the inner element, which drives up the price of the inner element and has given rise to the problem of a greater burden on the patient.

What is more, during prolonged wear silicone-rubber helmets through which cooling fluid flows often come to the brink of slipping off, wherein if the helmet gets out of place the cooling effect will be diminished. A cooling helmet that is a commercially available product is devised with a clasp, and with a belt fixes the user's chin and a portion of the helmet opening so as to prevent the helmet from shifting. With a fixing scheme of this sort, however, the snugness of the fit of the helmet onto the scalp cannot be ensured.

PRECEDENT TECHNICAL LITERATURE

Patent Document(s)

Patent Document 1: Japanese Patent No. 5,133,355

SUMMARY OF INVENTION

Issues Invention is to Address

Therein, in view of these sorts of problems, an issue for the present invention is to afford a medical head-cooling cap set that is constituted from three items being a head-cooling cap for cooling a user's head, an inner cap that fits on the inner side of the head-cooling cap, and a securing-gear-attached outer cap that is for securing, and that fits on the outer side of, the head-cooling cap, and that fitted on produces no pressuring feeling nor slips out of place.

Means for Resolving Issues

For solving the above-stated problems, a medical head-cooling cap set involving the present invention is constituted from three items being a head-cooling cap for cooling a user's head, an inner cap that fits on the inner side of the head-cooling cap, and a securing-gear-attached outer cap that is for securing, and that fits on the outer side of, the head-cooling cap, characterized in that: a cooling-medium flow path is formed in the interior of the head-cooling cap, the scalp being cooled by the circulating of a cooling medium in the cooling-medium flow path; the inner cap is made from a fabric component formed so as to cover a person's head, and is constituted from a main part furnished with a frontal region that covers the forehead including the brow, an occipital region that covers the occiput, and a nape region that covers the nape, and from a left temporal element and a right temporal element, connected to the main part, and further in a rear edge of each element of the left temporal element and the right temporal element connected to the main part a finlike protrusion is formed, and between the finlike protrusions and the nape region a slit is formed. The cap set is characterized in that two first belts that are drawn out from either side of the outer-cap opening part and stretch to the exterior are linkable by a first fastener, and after the head has been passed into the opening and the outer cap has been donned, the belts can be fastened neck-area-forward by means of the first fastener; and meanwhile, two second belts that extend from a rear middle part near the brim and run frontally along the brim are linkable by a second fastener, and after the head has been passed into the opening and the outer cap has been donned, the second belts can be fastened around the forehead by the second fastener. Here, the inner cap may be made furnished with a handle on an edge part of its frontal region. Further, constituting the outer cap by a foam-rubber elastic element, and a fiber-layer-containing elastic material disposed on obverse and reverse sides of the foam-rubber elastic element is optimal. Here, making the raw-material component of the foam-rubber elastic element consist of polychloroprene or neoprene (registered trademark) is further advantageous.

Also, a method, involving the present invention, of using a medical head-cooling cap set is characterized in: soaking in water, lightly wringing out, and fitting onto a user's head an inner cap; next, putting onto the inner cap a head-cooling cap for cooling the user's head; and further, putting onto the head-cooling cap a securing-gear-attached outer cap, and linking and securing at the neck area of the user two first belts that are drawn out from either side of the outer-cap opening part and stretch to the exterior, and meanwhile, linking and binding tight around the forehead by means of a second fastener two second belts that extend from a rear middle part near the brim and run frontally along the brim of the outer-cap; whereby displacement of the head-cooling cap is prevented and gaps between the head-cooling cap and the scalp are decreased, improving the cooling effectiveness of the head-cooling cap. Here, wetting the user's hair prior to fitting the inner cap onto the user is optimal.

Effects of Invention

A medical head-cooling cap set involving the invention, by preventing displacement of the head-cooling cap by means of a clasp on the outer cap, is made easier for the user to put on; its inner cap not only has a suitable degree of heat-insulating effectiveness, but may be gotten at reasonable cost to the user; and its outer cap, by means of the clasp, makes it possible to prevent displacement of the head-cooling cap Further, adopting a foam-rubber elastic element, and a fiber-layer-containing elastic material disposed on obverse and reverse sides of the foam-rubber elastic element for the material of the outer cap makes it possible to hold the head-cooling cap in place firmly, and to better prevent displacement of the head-cooling cap. Also, selecting from inner-cap sizes of several kinds makes it possible to adapt the cap set to persons of differing head size, yielding a stabilized wearing condition. Further, having cloth, nonwoven fabric, or the like be the material of the inner cap means that it is unlikely to degrade, and that the risk of it producing itching or rashes on the human body is minimal. Also, the inner cap may be made launder-and-reusable, or may be made disposable.

MODE(S) FOR IMPLEMENTING INVENTION

In the following, based on the drawings, a detailed description of embodiment examples of the present invention will be made. In each figure, identical parts are labeled with identical reference numbers, wherein reduplicating description will be omitted. Further, the drawings in some instances are expressed exaggeratedly for the sake of understanding the present invention, wherein it should be borne in mind that they are not necessarily scaled-down, minute representations. Furthermore, the invention is not limited to the embodiment examples illustrated below.

Embodiment Example 1

Embodiment Example 1 will be described in detail with reference to the drawings.

Figure 1:
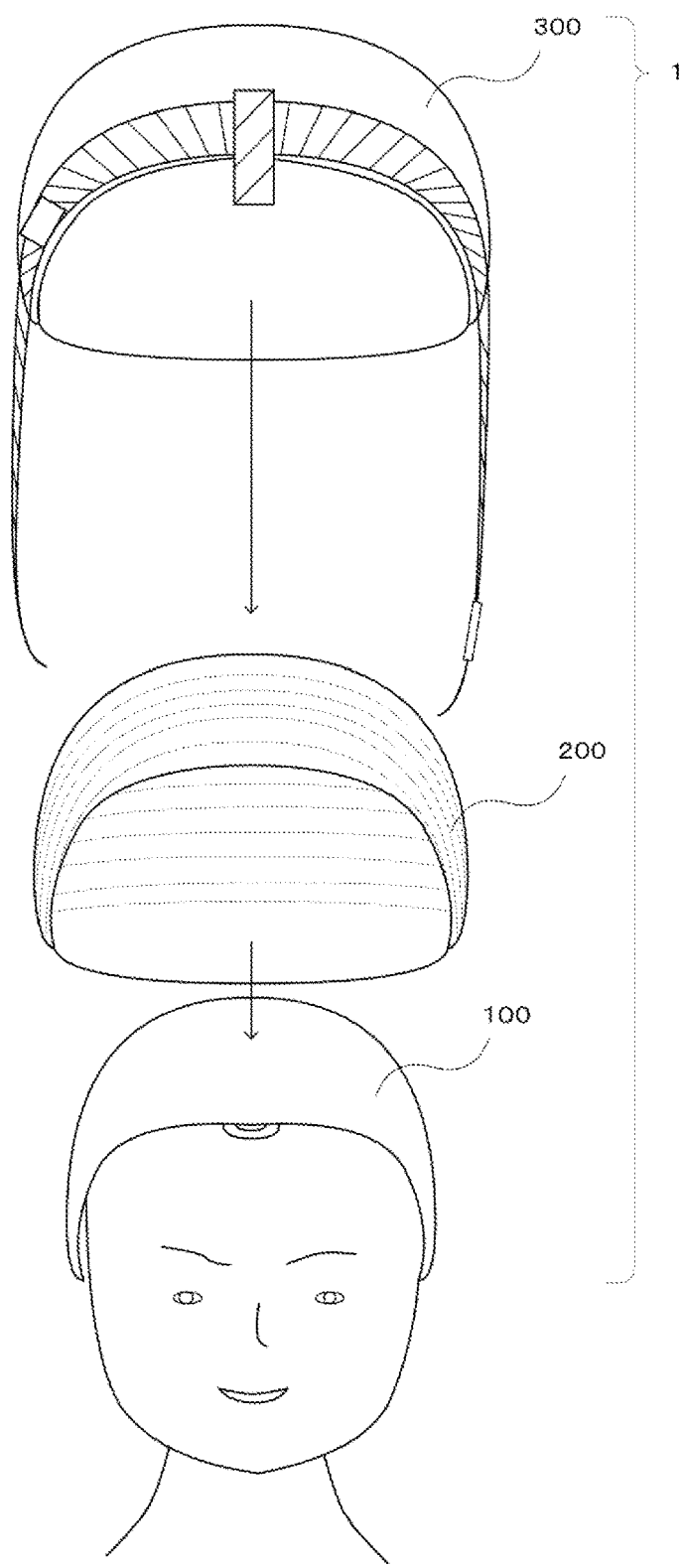
FIG. 1 is a view illustrating the configuration of a medical head-cooling cap set 1 involving the present invention.

Reference is made to FIG. 1. The figure is a view illustrating the configuration of a medical head-cooling cap set 1.

Figure 2:
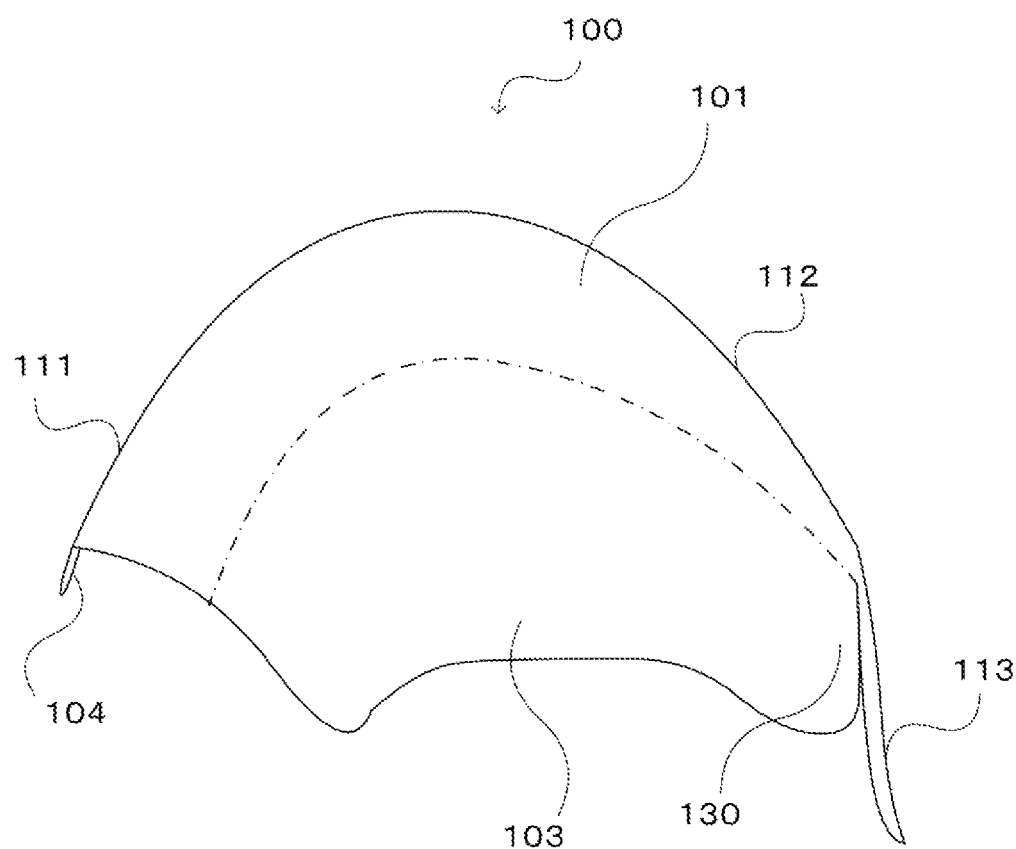
FIG. 2 is a right-side diagram of an inner cap 100 involving the present invention.

Reference is made to FIG. 2. FIG. 2 is a right-side view of the inner cap 100 according to the present invention. The main part 101 includes a frontal region 111, an occipital region 112, and a nape region 113. The main part 101 is sutured and made unitary with a left temporal piece 102 (not represented in the figure) along a sewn section, and with a right temporal piece 103 along a sewn section (indicated by dot-and-dash lines). It should be noted that the junctures between the main part 101, and the left temporal piece 102 and the right temporal piece 103 are not limited to sutures. The respective members that are the left temporal piece 102 and the right temporal piece 103 form finlike protrusions 120 and 130 at the rear end, wherein slits are formed between the finlike protrusions 120 and 130 and the nape region 113.

As illustrated in FIG. 2, the main part 101 may have a handle 104 attached to its front end, that is, an edge part of the frontal region 111. When a user In putting on the inner cap 100 and fits on the head-cooling cap 200, the user can correct displacement of the inner cap 100 by pulling the handle 104. Any article that allows its being gripped and pulled by a user is adequate for the handle 4; it may be an article in the form of a loop, and it may be a tongue-flap article as well, sewn onto the front end of the frontal region 111.

Here, any fabric component that has a suitable degree of heat-insulating effectiveness is adequate to be utilized for the inner cap 100. That is, any material that may be processed into the form of the inner cap 100 illustrated in FIGS. 1 and 2 is adequate. For example, as the fabric component, polyester or other chemical fiber is acceptable, while cotton, nonwoven fabrics, paper, or as materials other than these, silk, or plastics, etc. that are like thin cloth, can be selected.

The right temporal piece 103 is sewn together with the main part 101 at the upper end. The right temporal piece 103 has the finlike protrusion 130 formed at the rear end, and the slit formed between the finlike protrusion 130 and the nape region 113. A slit of this sort makes it possible to adapt the medical cap to persons of differing head sizes, yielding a stabilized wearing condition. The lower-end line of the right temporal piece 103 may be concavely curved so as not to cover the ear.

The inner cap 100 of the present invention, since it has a suitable degree of heat-insulating effectiveness, is ideal as an inner cap specialized for the head-cooling cap 200 for cooling the scalp, and when the inner cap 100 is put on and the head-cooling cap 200 is fitted over it, since it serves as a cushioning material between the head-cooling cap 200 and the scalp, it lends a comfortable fit to the user.

Figure 3:
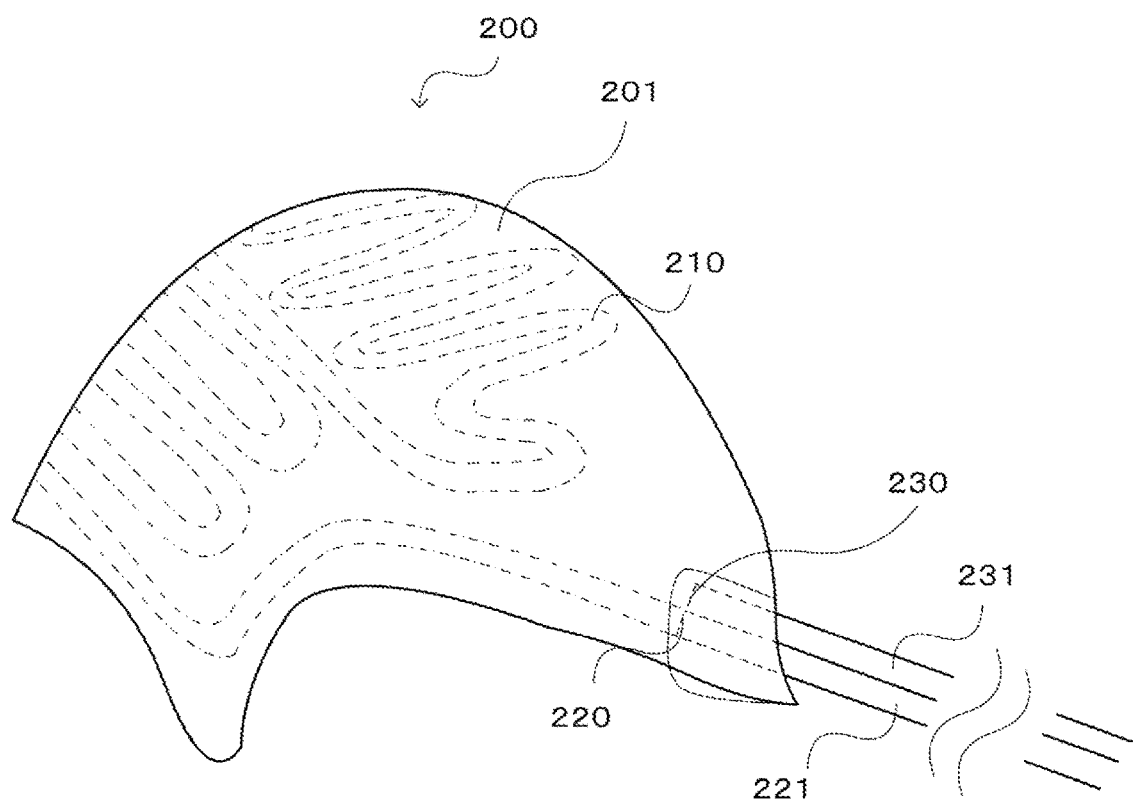
FIG. 3 is a right-side diagram of a head-cooling cap 200 involving the present invention.

Reference is made to FIG. 3. FIG. 3 is a right-side diagram of a head-cooling cap 200 involving the present invention. The head-cooling cap 200 is provided with a first cooling-medium port 220 and a second cooling-medium port 230, wherein respectively connected to the ports are lines 221 and 231 for supplying and discharging cooling medium.

In the head-cooling cap main part 201 of the head-cooling cap 200, a cooling-medium flow path 210 extending between the first cooling medium port 220 and the second cooling medium port 230 is formed, and is disposed so that cooling medium supplied into the head-cooling cap main part 201 interior can circulate inside the cooling-medium flow path 210. The head-cooling cap 200 is cooled by cooling medium circulating in the cooling-medium flow path 210, and as a result, by heat exchange with the scalp of a user on whom the head-cooling cap 200 is fitted, the user's scalp is cooled.

Figure 4:
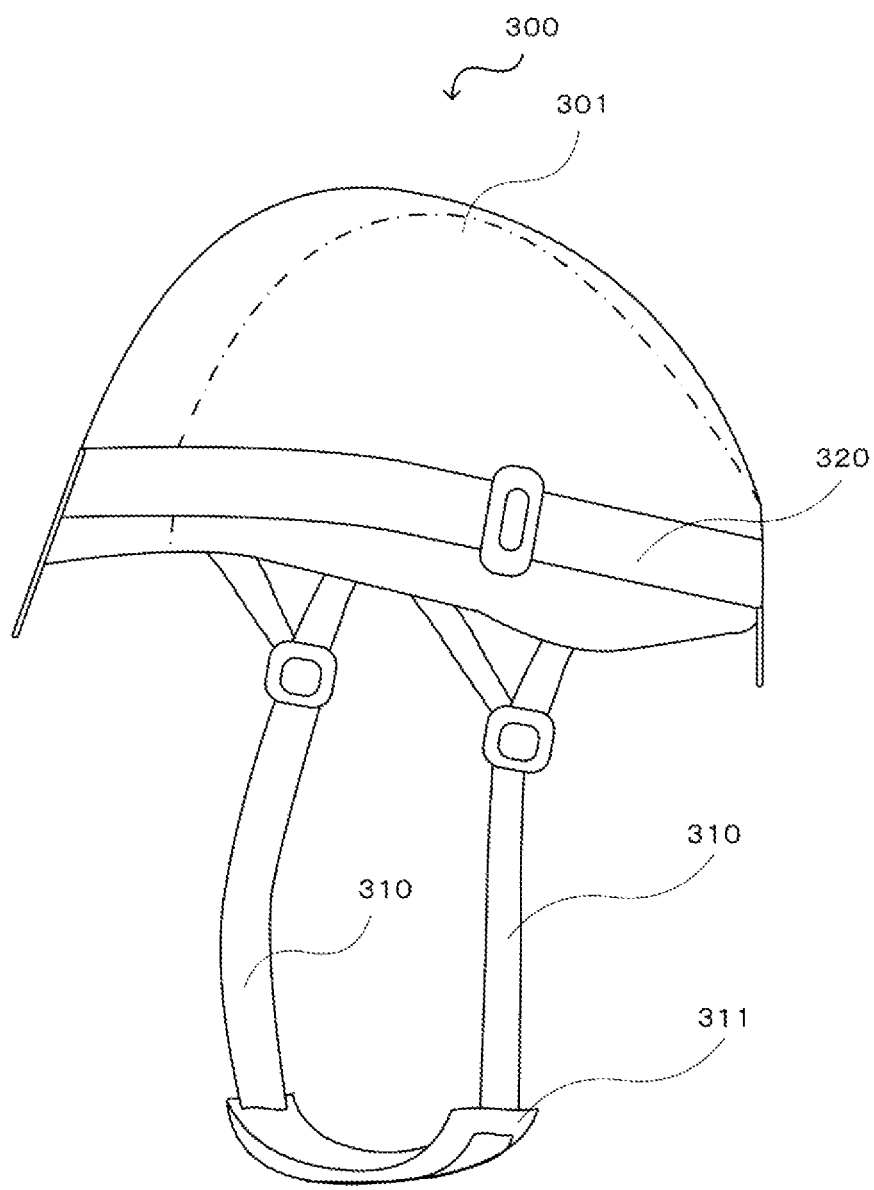
FIG. 4 is a view illustrating an outer cap 300 involving the present invention.

Reference is made to FIG. 4. FIG. 4 is a view illustrating an outer cap 300 involving the present invention. The outer cap 300 is fitted onto the outer side of the head-cooling cap 200. The outer cap 200 is formed from a heat-insulating material such as urethane, and keeps the temperature of the cooling medium inside the head-cooling cap 200 from rising due to the influence of the external air temperature. The outer cap 300 is put onto the head-cooling cap 200, and with the user's neck area placed on a chin holder 311, is secured by coupling two first belts 310 that are drawn out from either side of the opening part and extend to the exterior. Then second belts 320 that extend from a rear middle part near the brim and run frontally along the brim are linked with a second fastener to bind them tight around the forehead. Doing that tightens the head-cooling cap 200 against the scalp, thereby decreasing the gap between the head-cooling cap 200 and the scalp, improving the cooling effectiveness, and further, demonstrating the advantage of preventing displacement of the head-cooling cap 200. If the head-cooling cap 200 shifts out of place, areas along the head where cooling to the scalp is not complete arise; consequently, it is necessary that displacement of the head-cooling cap be prevented to the utmost. Here, as the material used for the outer cap a heat-insulating substance such as urethane is adequate, but a material that does not let body heat escape, that is, a material that may maintain thermo-retentive properties/heat-insulating properties, and that securely fits on the head-cooling cap 200 and that has flexibility and elasticity is preferable. For example, a foamable rubber material, such as neoprene (registered trademark) and polychloroprene, to the obverse and reverse sides of which a woven or knitted fabric is affixed, or a material constituted by a base substance to which a textile is affixed is preferable. There is little difficulty in obtaining these sorts of materials, and from a cost perspective they are superior.

Embodiment Example 2

Figure 5:
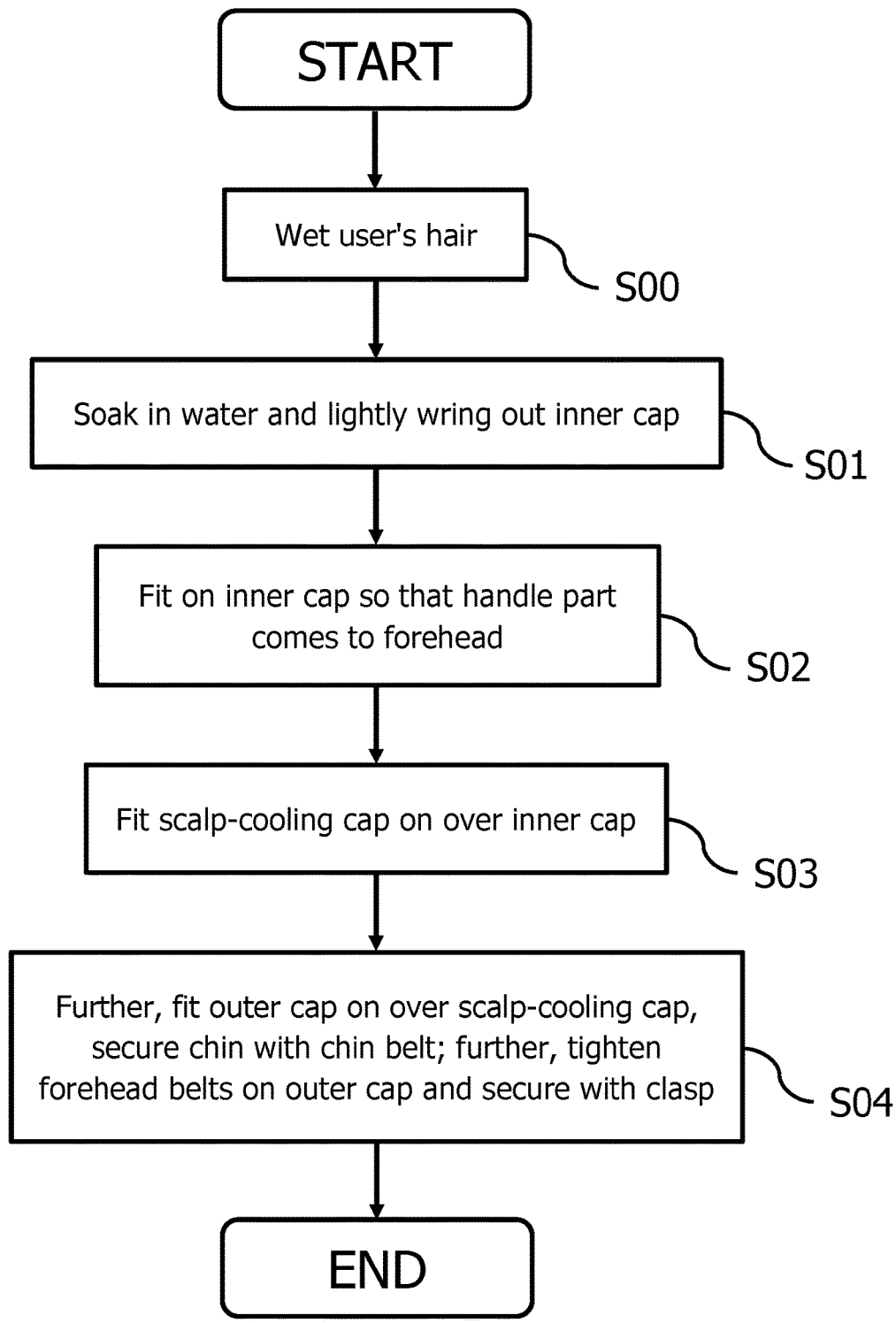
FIG. 5 is a flowchart representing a method of using a medical head-cooling cap set 1 involving the present invention.

Embodiment Example 2 will be described in detail with reference to the drawings. FIG. 5 is a flowchart illustrating a method of using a medical head-cooling cap set 1 involving the present invention.

With reference to FIG. 5, an explanation of a method of using a medical head-cooling cap set involving the present invention will be made. To begin with, the inner cap 100 is soaked in water and lightly wrung out (S01), and then fitted on a user's head (S02). Here, before the inner cap 100 is fitted on a user's head, it is recommendable to wet the user's hair (S00); wetting it with a sprayer or the like about till water drips out is further recommendable. Also, when the inner cap 100 is fitted on the user's head, in instances, for example, in which hair loss on the top of the head is conspicuous, placing gauze on the top of the head and then fitting on the inner cap 100 is recommendable. Further, in order that the head-cooling cap 200 not come into direct contact with the frontal region, ears, etc., it is recommendable to cover those places with gauze before fitting on the inner cap 100. Next, the head-cooling cap 200 for cooling the user's head (S03) is put onto the inner cap 100. The head-cooling cap 200 is put so as not to be to the front of the inner cap 100. This is because there is a risk of the scalp being frostbitten if the head-cooling cap 200 directly touches it. After the head-cooling cap 200 is fitted on the user, in order that the head-cooling cap 200 be made snug against the head, it is recommendable that the user him/herself or a caregiver press the head-cooling cap 200 down. This is because poor snugness of fit dilutes the scalp-cooling effectiveness. Then, the securing-gear-attached outer cap 300 is put onto the head-cooling cap 200 (S04). At this point, turning the outer cap 300 inside out, aligning the forehead side with the user's brow, and sliding the left and right rear of the outer cap 300 along the user's head is recommendable. There should be no gaps between the head-cooling cap 200 and the outer cap 300. Next, the two first belts that are drawn out from either side of the opening part and extend to the exterior are linked and secured at the user's neck area, and the two second belts that extend from a rear middle part near the brim and run frontally along the brim are linked by means of the second fastener and bound tight around the forehead. Here, for a user with a large head size, it is recommendable that the user him/herself or a caregiver press the outer cap 300 down against the head. The presence of the outer cap 300 prevents displacement of the head-cooling cap 200.

Embodiment Example 3

Embodiment Example 3 will be described with reference to the table.

The applicant in the present application conducted tests to ascertain the effects of an outer cap involving the present invention. The tests were executed internally at Taiyou Industries Co., Ltd. (682 Higashiyama, Sakai-shi Naka-ku, Osaka) head-office factory in Sakai City, on Jan. 16, 2020.

Key points of implementation: With an inner cap, head-cooling cap, and outer cap involving the present invention fitted on a test subject, a temperature sensor was placed on the inner side of the inner cap (the part in contact with scalp hair), and the temperature was measured with the temperature sensor. On the other hand, measurement was made by said temperature sensor with the below-described, commercially available helmet fitted over a head-cooling cap involving the present invention, and was compared with the temperature in the instance in which the outer cap involving the present invention had been fitted on. It should be noted that the outer cap is fitted with a chin pad, and straps for tightening against the sides. Here, the outer cap is composed from a base medium in which the foamable rubber material neoprene is utilized as a raw-material component, and on its obverse and reverse sides a woven/knitted fabric is attached, or a textile is attached.

Measurement protocol: From the point in time at which the scalp temperature attained near fixity (after by and large a 10-minute lapse from the start of post-fitting cooling) (1) the scalp temperature was measured for approximately 30 minutes with an outer cap involving the present invention having been fitted on.

(2) The scalp temperature was measured for approximately 30 minutes with the helmet, instead of the outer cap, having been fitted on. It is to be noted that with the temperature measurements, the data was automatically logged (collected) every minute by means of a data logger. A table presenting the temperatures and temperature differences for (1) and (2) is the table below.

As presented in the table, it will be understood that with the outer cap involving the present invention and the helmet, the temperatures in which the outer cap was fitted on was maintained low throughout the entirety. With the average temperature differences being 0.57° C. at the frontal area and 1.51° C. at the right head area, the outer cap being worn sustained lower than the helmet being worn.

From the foregoing results, it can be appreciated that with an outer cap involving the present invention is the benefit that the effect of cooling the scalp by means of the head-cooling cap is maintained.
Measurement date and time: Jan. 16, 2020, from around 13:00 to around 15:00
Room temperature: 26.9° C.
Humidity: 21%
Measurement location: Taiyou Industries Co., Ltd. (Sakai-shi, Osaka)
Helmet
   Sales agency: Midori Anzen Co., Ltd.
   Model: light work cap SCL-100A
   Product number: L100N White SCL100N-03G-3
   Material: PE (Polyethylene)
It should be noted that the helmet was employed with the chin-pad attachment removed so that it could be fitted on over the head-cooling cap.
Measurement points: 2 points, forehead area and right head area
Thermometer used: Sato Shoji Inc., two TM-947SDs (one thermometer has 4 channels)
Sensor used: K thermocouple
Time units: minutes From the foregoing results, it can be appreciated that with an outer cap involving the present invention is the benefit that the effect of cooling the scalp by means of the head-cooling cap is maintained.
Measurement date and time: Jan. 16, 2020, from around 13:00 to around 15:00
Room temperature: 26.9° C.
Humidity: 21%
Measurement location: Taiyou Industries Co., Ltd. (Sakai-shi, Osaka)
Helmet
   Sales agency: Midori Anzen Co., Ltd.
   Model: light work cap SCL-100A
   Product number: L100N White SCL100N-03G-3
   Material: PE (Polyethylene)
It should be noted that the helmet was employed with the chin-pad attachment removed so that it could be fitted on over the head-cooling cap.
Measurement points: 2 points, forehead area and right head area
Thermometer used: Sato Shoji Inc., two TM-947SDs (one thermometer has 4 channels)
Sensor used: K thermocouple
Time units: minutes

TABLE

| Elapsed time | ch1 Outer cap Front | ch1 Helmet Front | Difference | ch4 Outer cap Right | ch4 Helmet Right | Difference |
|---|---|---|---|---|---|---|
| 0 | 16.6 | 16.8 | −0.2 | 21.2 | 23.0 | −1.8 |
| 1 | 16.5 | 16.7 | −0.2 | 21.2 | 23.0 | −1.8 |
| 2 | 16.3 | 16.7 | −0.4 | 21.1 | 22.9 | −1.8 |
| 3 | 16.1 | 16.8 | −0.7 | 21.0 | 23.0 | −2.0 |
| 4 | 16.1 | 17.0 | −0.9 | 21.0 | 23.1 | −2.1 |
| 5 | 16.2 | 17.0 | −0.8 | 21.1 | 23.2 | −2.1 |
| 6 | 16.2 | 17.0 | −0.8 | 21.2 | 23.3 | −2.1 |
| 7 | 16.3 | 17.0 | −0.7 | 21.2 | 23.2 | −2.0 |
| 8 | 16.2 | 16.8 | −0.6 | 21.3 | 23.1 | −1.8 |
| 9 | 16.1 | 16.8 | −0.7 | 21.3 | 22.9 | −1.6 |
| 10 | 16.1 | 16.8 | −0.7 | 21.3 | 22.9 | −1.6 |
| 11 | 16.1 | 17.0 | −0.9 | 21.3 | 23.0 | −1.7 |
| 12 | 16.2 | 17.1 | −0.9 | 21.4 | 23.1 | −1.7 |
| 13 | 16.3 | 17.1 | −0.8 | 21.5 | 23.1 | −1.6 |
| 14 | 16.4 | 17.0 | −0.6 | 21.7 | 23.1 | −1.4 |
| 15 | 16.4 | 16.8 | −0.4 | 21.7 | 22.9 | −1.2 |
| 16 | 16.3 | 16.8 | −0.5 | 21.7 | 22.9 | −1.2 |
| 17 | 16.3 | 16.7 | −0.4 | 21.7 | 22.9 | −1.2 |
| 18 | 16.3 | 16.8 | −0.5 | 21.7 | 22.9 | −1.2 |
| 19 | 16.3 | 17.0 | −0.7 | 21.8 | 23.0 | −1.2 |
| 20 | 16.5 | 17.1 | −0.6 | 21.9 | 23.1 | −1.2 |
| 21 | 16.6 | 17.0 | −0.4 | 21.9 | 23.1 | −1.2 |
| 22 | 16.6 | 17.0 | −0.4 | 22.0 | 23.1 | −1.1 |
| 23 | 16.6 | 16.9 | −0.3 | 22.2 | 23.1 | −0.9 |
| 24 | 16.6 | 16.9 | −0.3 | 22.1 | 23.2 | −1.1 |
| 25 | 16.4 | 16.9 | −0.5 | 22.1 | 23.2 | −1.1 |
| 26 | 16.4 | 17.0 | −0.6 | 22.0 | 23.2 | −1.2 |
| | | Average | −0.57 | | | −1.51 |

In the foregoing, preferred embodying modes in medical head-cooling cap sets involving the present invention have been illustrated and explained; however, it should be understood that a variety of modifications are possible without departing from the technical scope of the present invention.

INDUSTRIAL EXPLOITABILITY

A medical head-cooling cap set involving the present invention is broadly exploitable not only in the medical arena, but also including situations in which cooling of the scalp is carried out at home, because the cap set is made easy for a user to wear by its preventing, by means of the clasps on the outer cap, the head-cooling cap from shifting out of place, and because not only does the inner cap have a suitable degree of heat-insulating effectiveness, it also may be acquired at an affordable cost for the user.

DESCRIPTION OF REFERENCE MARKS

1: Medical head-cooling cap set
100: Inner cap
101: Inner cap main part
111: Frontal region
112: Occipital region
113: Nape region
102: Left temporal piece
103: Right temporal piece
120, 130: Finlike protrusion
104: Handle
200: Head-cooling cap
201: Head-cooling cap main part
210: Cooling-medium flow path
220: First cooling medium port
230: Second cooling medium port
221: Pipe
231: Pipe
300: Outer cap
301: Outer cap main part
310: Chin belt
311: Chin holder
320: Forehead belt

The invention claimed is:
1. A medical head-cooling cap set constituted from three items being a head-cooling cap for cooling a user's head, an inner cap that fits inside the head-cooling cap, and an outer cap that is for securing, and that fits outside, the head-cooling cap, characterized in that:

a cooling-medium flow path is formed interiorly in the head-cooling cap, the head-cooling cap therein being adapted for cooling the user's scalp by a cooling medium being circulated in the cooling-medium flow path; and the inner cap is made from a fabric component formed so as to cover the user's head, and is constituted from a main part furnished with a frontal region that is adapted to cover the user's forehead including the brow, an occipital region that is adapted to cover the user's occiput, and a nape region that is adapted to cover the user's nape, and a left temporal element and a right temporal element, connected to the main part, wherein a left finlike protrusion is formed in a rear edge of the left temporal element and a right finlike protrusion is formed in a rear edge of the right temporal element, and between each of the respective left and right finlike protrusions and the nape region a slit is formed; wherein the outer cap is adapted to receive, through a brim-defining opening therein, the user's head fitted with the head-cooling cap over the inner cap, and is configured with attached securing gear comprising two first belts that are drawn out from either side of the outer-cap opening and stretch to the exterior, and a first fastener for linking the two first belts, wherein after the user's head fitted with the head-cooling cap over the inner cap has been passed into the opening and the outer cap has been donned, the two first belts can be fastened neck-area-forward by means of the first fastener; and two second belts that extend from a rear middle part near the brim and run frontally along the brim, and a second fastener for linking the two second belts, wherein after the user's head fitted with the head-cooling cap over the inner cap has been passed into the opening and the outer cap has been donned, the two second belts can be fastened around the user's forehead by means of the second fastener.

2. The medical head-cooling cap set recited in claim 1, characterized in that the inner cap is furnished with a handle on an edge part of said frontal region.

3. The medical head-cooling cap set recited in claim 1, characterized in that the outer cap is constituted by a foam-rubber elastic element, and a fiber-layer-containing elastic material disposed on obverse and reverse sides of the foam-rubber elastic element.

4. The medical head-cooling cap set recited in claim 3, characterized in that the foam-rubber elastic element is of a raw-material component consisting of polychloroprene.

5. A method of using a medical head-cooling cap set, characterized in:

soaking in water, lightly wringing out, and fitting onto a user's head an inner cap;

next, putting onto the inner cap a head-cooling cap for cooling the user's head; and further, putting onto the head-cooling cap an outer cap with a brim-defining opening, and linking and securing at the neck area of the user two first belts, attached as securing gear to the outer cap, that are drawn out from either side of the outer-cap opening and stretch exteriorly, and meanwhile, linking and binding tight around the forehead by means of a fastener two second belts, attached as securing gear to the outer cap, that extend from a rear middle part near the brim and run frontally along the brim; whereby displacement of the head-cooling cap is prevented and gaps between the head-cooling cap and the scalp are decreased, improving cooling effectiveness of the head-cooling cap.

6. The medical head-cooling cap set use method recited in claim 5, characterized in that prior to the inner cap being fitted onto the user, the user's hair is wetted.

7. The medical head-cooling cap set recited in claim 2, characterized in that the outer cap is constituted by a foam-rubber elastic element, and a fiber-layer-containing elastic material disposed on obverse and reverse sides of the foam-rubber elastic element.

8. The medical head-cooling cap set recited in claim 7, characterized in that the foam-rubber elastic element is of a raw-material component consisting of polychloroprene.

* * * * *